United States Patent [19]

Bauer

[11] Patent Number: 4,675,036

[45] Date of Patent: Jun. 23, 1987

[54] PROCESS FOR THE SEPARATION OF $C_{2+}$ OR $C_{3+}$ HYDROCARBONS FROM A PRESSURIZED HYDROCARBON STREAM

[75] Inventor: Heinz Bauer, Neuried, Fed. Rep. of Germany

[73] Assignee: Linde Aktiengesellschaft, Wiesbaden, Fed. Rep. of Germany

[21] Appl. No.: 809,957

[22] Filed: Dec. 17, 1985

[30] Foreign Application Priority Data

Dec. 17, 1984 [DE] Fed. Rep. of Germany ....... 3445994

[51] Int. Cl.$^4$ ............................................... F25J 3/02
[52] U.S. Cl. ........................................... 62/18; 62/31; 62/34; 62/39
[58] Field of Search .................... 208/340, 341; 62/32, 62/33, 31, 34, 29, 11, 16, 38, 39

[56] References Cited

U.S. PATENT DOCUMENTS

| | | | |
|---|---|---|---|
| 2,880,592 | 4/1959 | Davison et al. | 62/39 X |
| 3,319,429 | 5/1967 | Pryor | 62/39 X |
| 3,516,261 | 6/1970 | Hoffman | 62/34 X |
| 3,622,504 | 11/1971 | Strum | 208/340 |
| 4,274,850 | 6/1981 | Becker | 62/38 X |
| 4,410,342 | 10/1983 | Horton | 62/39 X |
| 4,453,956 | 6/1984 | Fabbri et al. | 62/34 X |
| 4,456,461 | 6/1984 | Perez | 62/34 X |
| 4,479,871 | 10/1984 | Panade et al. | 208/340 |
| 4,486,209 | 12/1984 | Fabbri et al. | 62/34 X |
| 4,519,824 | 5/1985 | Huebel | 62/34 X |

Primary Examiner—Andrew H. Metz
Assistant Examiner—Glenn A. Caldarola
Attorney, Agent, or Firm—Millen & White

[57] ABSTRACT

A low temperature rectification process for obtaining $C_{2+}$ or $C_{3+}$ hydrocarbons from feed gas mixtures, which contain essentially light hydrocarbons and, if desired, hydrogen or nitrogen is shown. The gas mixture is first cooled and subjected to phase separation, whereupon the gaseous fraction is work expanded and the liquid fraction is fractionated by rectification. The light overhead fractionated product of the rectification is mixed with the gaseous fraction of the phase separation of the feed gas mixture before its work expansion.

25 Claims, 4 Drawing Figures

PROCESS FOR THE SEPARATION OF $C_{2+}$ OR $C_{3+}$ HYDROCARBONS FROM A PRESSURIZED HYDROCARBON STREAM

CROSS REFERENCE TO RELATED APPLICATIONS

This application is related to concurrently filed and commonly assigned applications entitled: "Separation of $C_{3+}$ Hydrocarbon by Absorption and Rectification", Sapper, Ser. No. 809,953; "Process for Separation of $C_{2+}$, $C_{3+}$ or $C_{4+}$ Hydrocarbons", Ser. No. 809,956; and "Process for Separation of $C_{2+}$ or $C_{3+}$ Hydrocarbons", Bauer, Ser. No. 809,958, all applications being incorporated by reference herein.

BACKGROUND OF THE INVENTION

This invention relates to a process for the separation of $C_{2+}$ or $C_{3+}$ hydrocarbons from a feed gas stream containing light hydrocarbons in which the feed gas stream under a superatmospheric pressure is cooled, partially condensed and separated into a liquid and a gaseous fraction and in which the gaseous fraction is work expanded and the liquid fraction is fractionated by rectification into a product stream containing substantially all the $C_{2+}$ or $C_{3+}$ hydrocarbons, and a residual gas containing lower boiling components. By "light hydrocarbons" is meant a mixture of methane and at least $C_{2-3}$ hydrocarbons. The feed gas may also contain components boiling lower than methane, e.g., nitrogen.

Such processes are frequently used for the separation of ethane and/or propane from natural gases or other hydrocarbon gases, for example, refinery tail gas. Furthermore, these processes are suitable for the separation of similar unsaturated hydrocarbons, for example, ethylene or propylene, assuming these components are contained in the gas stream to be fractionated, such as in a refinery tail gas. The reprocessing of refinery tail gas has recently become economically attractive since market prices for LPG ($C_3/C_4$ hydrocarbon mixture) have risen, while on the othr hand vacuum residues and heavy oil are hard to sell. For this reason, the difficult to market heavy products are burned to cover the internal fuel needs of a refinery, while the easily marketable $C_{3+}$ hydrocarbons are separated from the tail gas which, in particular, is evolved in large amounts during the processing of light crude oil components into gasoline.

Such a process which relates to the separation of $C_{3+}$ hydrocarbons has already been described in German Patent Application No. P 34 08 760.5, filed Mar. 9, 1984 in Germany having a common assignee and corresponding substantially to U.S. application Ser. No. 709,742 filed Mar. 8, 1985 by Bauer et al, said U.S. application being incorporated by reference herein.

An essential feature of this German application is in the fact that the refrigeration obtained during work expansion of the gaseous fraction which remains after partial condensation is used not for the production of reflux liquid in the rectification column, but for cooling and partial condensation of the crude gas. Therefore, it is unnecessary to feed the light components of the gas stream into the rectification column. The elimination of the introduction of the light components present in the feedstock stream, particularly hydrogen, as well as $C_1$ and if desired, the $C_2$ hydrocarbons present in refinery gases; nitrogen, as well as $C_1$ and, if desired, $C_2$ hydrocarbons in natural gases into the rectification column makes it possible to perform the rectification at a higher temperature. The possibility of using a simple and economic cycle of external refrigeration for cooling of the overhead produced in the rectification stage indeed means a considerable improvement in carrying out the process, but yet additional improvement is desirable, nonetheless.

SUMMARY OF THE INVENTION

Therefore, an object of one aspect of the invention is to provide an improved process of the aforementioned type wherein the separation of the $C_{2+}$ or $C_{3+}$ hydrocarbons is made possible in a more economical manner.

Upon further study of the specification and appended claims, further objects and advantages of this invention will become apparent to those skilled in the art.

These objects are achieved by an improved process of the aforementioned type wherein the residual gas stream collecting overhead in the rectification column is fed into and mixed with the gaseous fraction formed from partial condensation of the feed gas; the mixture formed thereby is work expanded, e.g., in a turbine, and then heated in a heat exchanger, preferably in indirect heat exchange with the gas stream that is to be work expanded.

In a broad aspect, the invention comprises a process for the separation of $C_{2+}$ or $C_{3+}$ hydrocarbons from a gas stream containing light hydrocarbons and, if desired, of components boiling at a lower temperature than methane, in which the feed gas stream being under an elevated pressure is cooled, partially condensed and separated into a liquid and a gaseous fraction, whereupon the gaseous fraction is work expanded and the liquid fraction is fractionated by rectification into a product stream containing substantially all $C_{2+}$ or $C_{3+}$ hydrocarbons and a residual gas stream comprising lower boiling components than $C_2$, and wherein the improvement comprises passing the residual gas stream into the gaseous fraction resulting from the partial condensation whereby the mixture formed thereby is work expanded, and then heating resultant work expanded mixture by indirect heat exchange in a heat exchanger.

In contrast to the prior art process wherein the residual gas from the rectification column overhead is expanded into the work expanded stream and with it is heated either together or separately against the gas stream that is to be fractionated, a mixing of these two gas streams occurs, in the process of the invention, before the work expansion stage. Therefore, not only is a greater refrigeration output obtained by the work expansion of the residual gas from the rectification column than by the previously usual simple expansion in a throttling valve, but also, by the admixture of the residual gas before work expansion of the gaseous fraction separated from the condensed gas stream, an improved efficiency, e.g., of the expansion turbine usually utilized for this operation is obtained. This is believed due to the fact that the residual gas from the rectification column overhead exhibits a higher molecular weight than the gaseous fraction from the partial condensation step, although applicant does not wish to be bound by this theory.

After separation of the feed gas stream into the liquid fraction and gaseous fraction, e.g., in a phase separator, the gaseous fraction is at the dew point, just as is the residual gas removed as overhead from the rectification column. With the mixing of these two fractions, each at its dew point, a condensate is generally formed and it is preferred to separate the condensate before the work expansion of the gas to assist in the reliable operation of the expansion turbine.

The rectification column conditions, i.e., pressure and temperature, in obtaining the desired stream of $C_{2+}$ or $C_{3+}$ hydrocarbons are usually adjusted on the basis of a variety of limiting parameters, particularly with regard to the composition of the mixture that is to be rectified. Further, the feed gas mixture that is to be fractionated can also be made available under a variety of conditions, particularly significant variations in high pressure, e.g., from about 10 to 40 bar. In particular, it is within the scope of the invention that the separation process is so performed under conditions in which the pressure in the rectification column is either higher or lower than the pressure of the partially condensed gas stream passed to it from the phase separator.

In another embodiment of the process of the invention, if the rectification takes place at a higher pressure than the pressure of the partially condensed gas stream, the liquid fraction leaving the phase separator is pumped to the rectification pressure and the residual gas formed during rectification is expanded in a separator for the separation of the liquid from the gaseous fraction before the gaseous phase is mixed with the uncondensed crude gas in the phase separator. This embodiment of the process is particularly advantageous since, on the one hand, no compression of the gas stream itself is required, owing to the use of the less expensive pumping of the liquid fraction to the higher rectification pressure and, on the other hand, the expansion of the residual gas from the rectification column into the crude gas separator facilitates the separation of the condensate collecting during mixing, without other stages being necessary.

To avoid condensate formation during mixing, one of the particular streams to be mixed, or the mixture, can be sufficiently heated so that the resultant mixture temperature is not below the dew point. Heating can be performed, e.g., against crude gas that is to be cooled.

In another embodiment, if the rectification is performed at a lower pressure than the pressure of the partially condensed feed gas stream, it is provided that the gaseous fraction phase separated from the gas stream that is to be fractionated is expanded to the pressure of the residual gas stream, e.g., via a throttling valve, before the mixing takes place.

In yet another embodiment involving the processing of gas streams which are rich in components boiling lower than methane, an enrichment of these components can take place whereby they are separated from the $C_1$ and $C_2$ hydrocarbons by a further partial condensation before the work expansion of the gaseous fraction. This process technique can be used, for example, in the separation of $C_{2+}$ or $C_{3+}$ hydrocarbons and of nitrogen from nitrogen-rich natural gas or, particularly, for the separation of said heavy hydrocarbons and of hydrogen from hydrogen-rich refinery gases. Such a separation is especially advantageous if the feedstock stream exhibits a relatively high portion of low-boiling components, for example, a hydrogen content on an order of magnitude of 50 to 90%. Such an amount of hydrogen is sufficient to produce in the expansion turbine the refrigeration needed for the additional separation without additional external refrigeration being necessary.

In many applications, a further fractionation of the $C_{2+}$ or $C_{3+}$ hydrocarbon products, particularly a separation between a $C_3/C_4$ hydrocarbon mixture and the $C_{5+}$ hydrocarbons is desired. For this purpose, according to another preferred embodiment, before the formation of the separated liquid phase and gaseous fractions, the major part of the $C_{5+}$ hydrocarbon fraction is separated from the gas stream, provided the concentration of these components is great enough that such a separation is economic.

The $C_{5+}$ separation advantageously takes place by partial condensation at a temperature of, e.g., about 240° to 280° K., that is above the temperature at which the above-named liquid liquid and gaseous fractions form. By the upstream separation of the heavy components, the mixture fed to the rectification column is almost free of $C_{5+}$ hydrocarbons, so that in the following rectification of the liquid fraction, a product stream is obtained, which in a $C_{3+}$ separation forms a commercial LPG fraction.

To riase the yield of $C_3$ and $C_4$ hydrocarbons, it is proposed, in a further embodiments of the process, that the separated $C_{5+}$ hydrocarbons also be fed to the same rectification column at an equilibrium point in the column below the feed of the $C_3$ and $C_4$ fraction. It is further provided that an intermediate column product stream containing essentially $C_3$ and $C_4$ hydrocarbons is removed between the two feeds. By the additional rectification of the $C_{5+}$ fraction, the $C_3/C_4$ hydrocarbons, which have condensed or are dissolved in the liquid phase during the formation of the $C_{5+}$ fraction by partial condensation, are also recovered as a product. Between the two feed locations a region of maximum $C_3/C_4$ concentration is formed in the rectification column, where the $C_3/C_4$ product stream is advantageously removed.

In a still further embodiment the gaseous fraction collecting after partial condensation of the raw feed is further cooled, e.g., in a heat exchanger, before the work expansion by indirect heat exchange with the work, e.g., turbine expanded fraction; in this case the additional components condensing out are separated before the work expansion stage. In this variation, the work expanded fraction is not immediately heated by contacting the gas stream that is to be fractionated in a suitable heat exchanger, but first is heated only with the uncondensed portion of the gas stream. Thus, the desired refrigeration produced in the work expansion is introduced into the gaseous fraction and contributes in a particularly efficient way to increased condensate formation, thereby leading to a higher yield of recovered $C_{2+}$ or $C_{3+}$ hydrocarbons. This embodiment is particularly effective in avoiding subcooling of the condensed portions of the gas stream to be fractionated which is energy inefficient.

In a preferred variation of this embodiment of the invention, the indirect heat exchange between the unexpanded and expanded gaseous fractions is performed in a mass transfer column having at least two and preferably about 2 to 5 equilibrium stages. Separation of the liquid fraction formed during partial condensation also takes place in this column, whereby the partially condensed gas stream is fed to the lower region of this column and the heat exchange between the unexpanded and expanded gaseous fraction takes place in the upper region of the column. The feed of the partially condensed gas stream into the lower region of the column provides heat to the bottom of the column, as a result of which the dissolved light components are at least partially stripped. The heat exchange occurring in the column head between the cold, expanded fraction, e.g., at about 160° to 240° K., and the unexpanded gaseous fraction results in a cooling of the column head, which further results in an increased condensation of the higher boiling components of the gaseous fraction and thus in a better yield.

BRIEF DESCRIPTION OF THE DRAWINGS

Various other objects, features and attendant advantages of the present invention will be more fully appreciated as the same becomes better understood when considered in connection with the accompanying drawings, in which like reference characters designate the same or similar parts throughout the several views, and wherein.

DETAILED DESCRIPTION OF THE DRAWINGS

Figure 1:
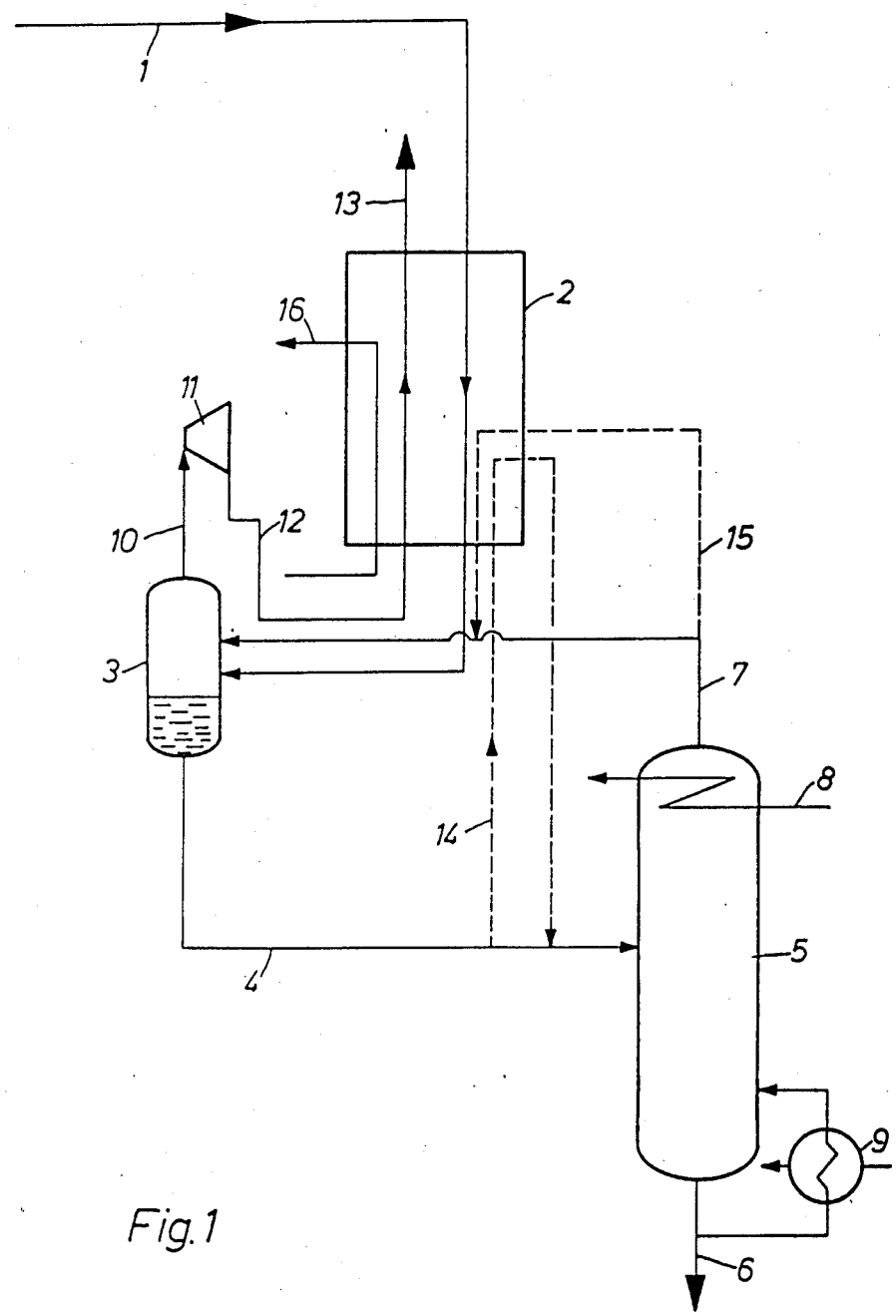
FIG. 1 is a simplified sketch of the process, wherein the rectification column and the phase separator are at substantially equal pressures.

In the embodiment shown in FIG. 1, 1, the gas stream to be fractionated under elevated pressure, e.g., about 10 to 40 bars and at approximately ambient temperature is fed by pipe 1 to heat exchanger 2, wherein it is cooled to, e.g., about 160° to 250° K., preferably about 175° to 235° K., so that most of the hydrocarbons to be separated, e.g., the $C_{2+}$ or $C_{3+}$ hydrocarbons are condensed. The partially condensed gas stream is subjected to a gas and liquid phase separation in phase separator 3, after which the formed condensate is fed by pipe 4 to a recification column 5 maintained at a pressure of about 10 to 40 bar, in which it is fractionated into a $C_{2+}$ or $C_{3+}$ fraction, which is removed as a product stream by pipe 6 from the column bottoms, and into an overhead residual gas stream 7 containing the lower boiling components. The rectification process is performed with the use of cooling facility 8 in the head of the column supplied through external refrigeration, e.g., at about 160° to 260° K., as well as with a bottoms reboiler 9 heated by low pressure steam, hot water, hot oil or other heat transfer fluids.

The overhead product of the rectification column is removed by pipe 7, and substantially comprises components which boil below the product fraction, i.e., the $C_{2+}$ or $C_{3+}$ fraction removed by pipe 6. This overhead stream is fed into phase separator 3 and mixed with the gaseous fraction of the crude gas which remains after the earlier partial condensation of the crude feed gas. The condensate which forms during the mixing step is removed in phase separator 3, so that a substantially liquid-free gas mixture remains and is removed in pipe 10, e.g., at a temperature of 160° to 250° K. and fed to expansion turbine 11. After the work expansion in turbine 11, the turbine exhaust gas at about e.g., 120° to 230° K. and 3 to 20 bar is passed via pipe 12 into heat exchanger 2 and is heated to about, e.g., 270° to 330° K., cooling the crude gas mixture that is to be fractionated. Finally, resultant heated gas exits through pipe 13 at about 270° to 330° K. and 3 to 20 bar as a light fraction and, for example, can be used as fuel gas.

The streams removed by pipes 4 and 10 from phase separator 3 or by pipe 7 from rectification column 5, before their further processing, can, if desired be heated or cooled to a more suitable temperature level, which, for example, can take place in heat exchanger 2. This is indicated by dashed lines 14 or 15 for the streams in pipes 4 and 7. The external refrigeration requirement for the process is supplied in cold loop line 16 which provides the cooling required for the gas mixture in heat exchanger 2, in conjunction with certain cold process streams that are to be heated.

Figure 2:
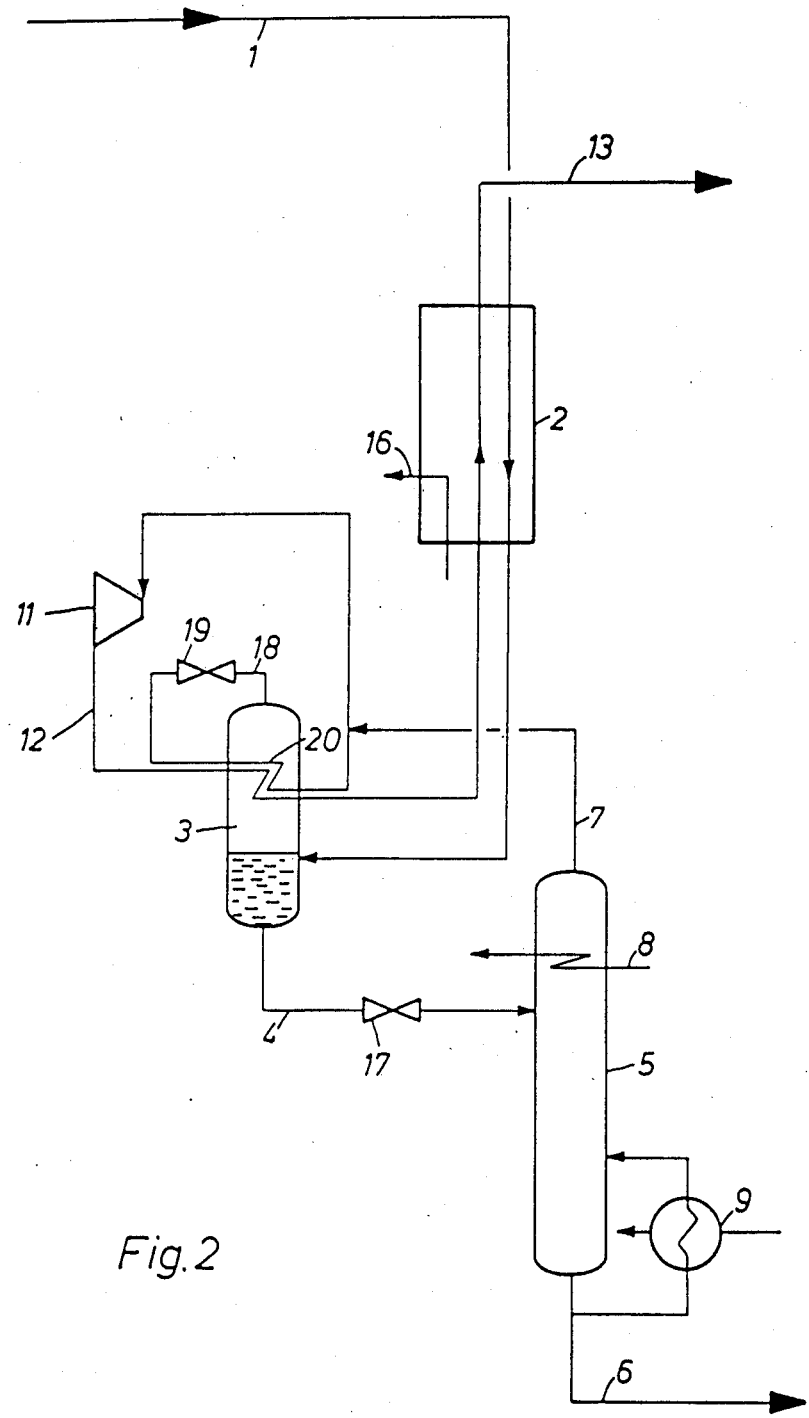
FIG. 2 discloses an embodiment of the process in which the pressure of the gas mixture to be fractionated is higher than the rectification column pressure.

In the embodiment shown in FIG. 2, the crude gas stream in pipe 1 which is to be fractionated is maintained at a relatively high pressure, e.g., 15 to 40 bar and 270° to 330° K. After separation of the formed condensate in phase separator 3, this liquid stream is expanded to the rectification pressure, e.g., about 10 to 35 bar, via a throttling valve 17 before being fed into rectification column 5. The gaseous fraction is removed from separator 3 by pipe 18, expanded in throttle valve 19 to the pressure of the residual gas in pipe 7 and, after being heated to about 170° to 250° K. in heat exchanger 20 by indirect heat transfer with the still unexpanded gaseous fraction, is mixed with the overhead gas stream from pipe 7, before the mixture, e.g., at about 165° to 255° K. and 10 to 35 bar, is fed to turbine 11. Thus, not only is the refrigeration from valve expansion 19 transferred to the gaseous fraction in phase separator 3, but also a useful heating of the throttled gas to above the dew point thereof occurs, e.g., about 5° to 40° K. above the dewpoint, so that no condensate formation takes place during the subsequent mixing with residual gas fraction 7. In the expansion of the gaseous stream in throttling valve 19, normally only a small pressure difference, e.g., about 1 to 5 bar is to be spanned so that here the use of a separate turbine is uneconomical. However, in the case of sufficiently large amounts of gas and larger pressure differences, the use of an expansion turbine is a suitable embodiment, thereby permitting use of the refrigeration thus available for increasing the yield or for decreasing the external cold requirement.

Before being subjected to heat transfer with the hot crude gas in heat exchanger 2, the gaseous mixture which was expanded in turbine 11 to about 140° to 230° K., is also heated in separator 3 to about 170° to 250° K., against the gaseous fraction therein. In this way, the desired peak refrigeration obtained via the turbine expansion is introduced into the heat exchanger 20 in phase separator 3, as a result of which the heavier hydrocarbons, e.g., $C_{2+}$ or $C_{3+}$ still contained in the gaseous fraction in the phase separator are substantially condensed without a subcooling of the condensate removed by pipe 4 occurring simultaneously.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Kelvin and all parts and percentages are by weight; unless otherwise indicated.

EXAMPLE I

In an embodiment according to FIG. 2, a refinery gas at a pressure of 29.2 bar and a temperature of 313° K. is introduced in pipe 1. It contains 12.2% hydrogen (indications of percent in each case refer to mol-%), 36.5 methane, 9.8% ethylene, 13.6% ethane, 13.6% propylene, 4.3% propane, 3.9% $C_{4+}$ hydrocarbons and 6.1% inerts (nitrogen, CO, $CO_2$). After cooling to 220° K. in heat exchanger 2 the gas, at a pressure of 29 bar, is separated from the condensed components in separator 3. The condensate removed by pipe 4 at a temperature of 220° K. contains 0.5% hydrogen, 18.2% methane, 14.7% ethylene, 23.2% ethane, 25.6% propylene, 8.1% propane, 7.5% $C_{4+}$ hydrocarbons and 2.2% inerts. It is expanded in valve 17 to the rectification pressure of 27 bar. Rectification is performed with a bottoms temperature of 346° K. and an overhead temperature of 250° K. In this case, in a $C_3$ bottoms product stream is obtained containing 1% ethane, 64.1% propylene, 19.5% propane and 18.1% $C_{4+}$ hydrocarbon. This stream contains 98.6% of the $C_3$ hydrocarbons fed by pipe 1. The rectification column contains 25 theoretical plates.

The residual overhead gas from the rectification column contains 0.9% hydrogen, 31.0% methane, 25.9% ethylene, 38.8% ethane, 0.5% $C_3$ hydrocarbons and 3.8% inerts. This residual gas stream is mixed with the gaseous fraction from separator 3, after said fraction was expanded in throttling valve 19 to a pressure of 27.2 bar and was heated in heat exchanger 20 to 207° K. in contact against the unexpanded fraction. After the work expansion, the mixture has a pressure of 6.5 bar and the turbine exhaust gas in line 12 is cooled to a temperature of 191° K. It is next heated against the gaseous fraction in phase separator 3 to 207° K. and finally heated to 310° K. against the crude gas to be cooled in heat exchanger 2, before it is delivered with a pressure of 5.7 bar.

Figure 3:
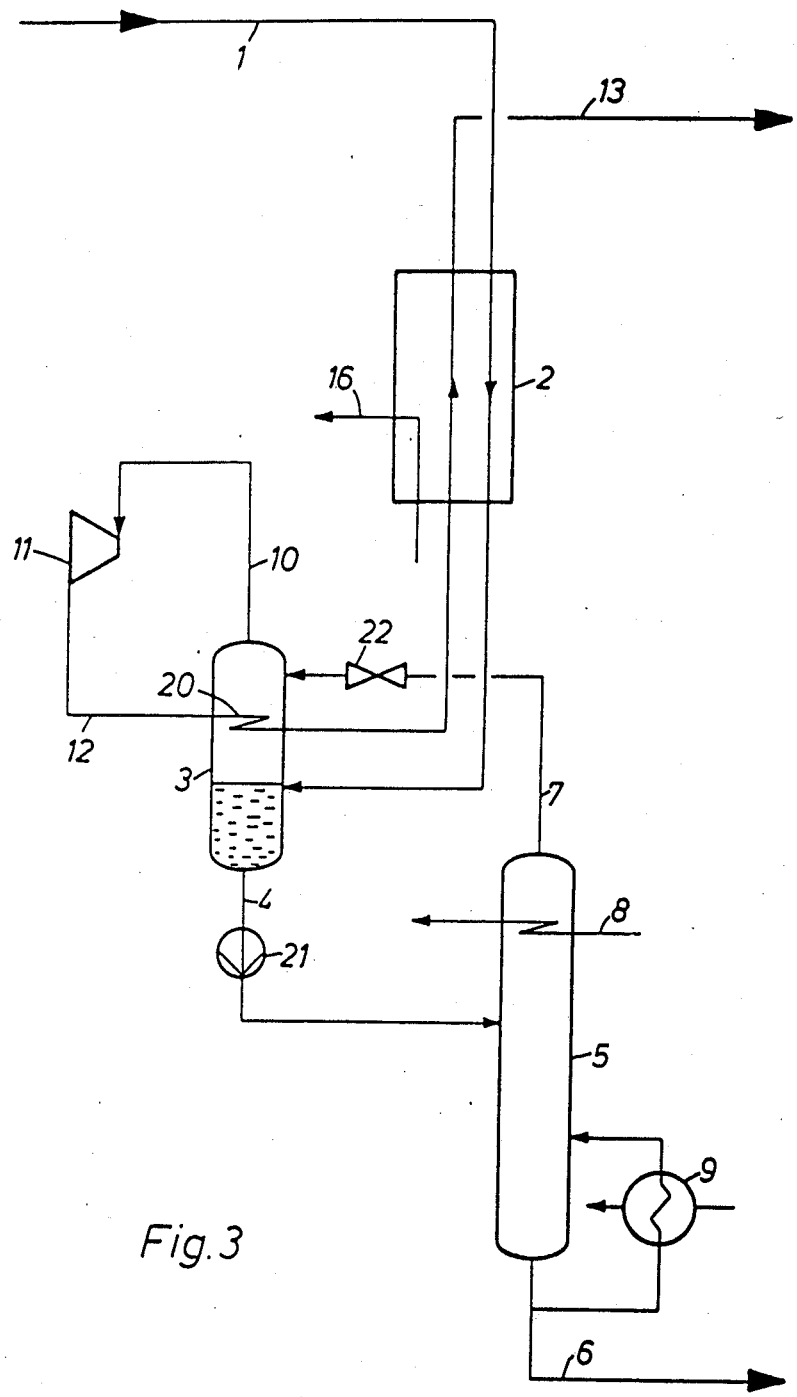
FIG. 3 discloses another embodiment of the invention in which the rectification column pressure is higher than the pressure of the gas mixture to be fractionated, and FIG. 4 discloses still another embodiment of the invention with a preseparation of $C_{5+}$ hydrocarbons.

The embodiment shown in FIG. 3 differs from the one in FIG. 2 by the fact that the rectification in column 5 is performed under a higher pressure, e.g., about 2 to 20 bar, than the pressure prevailing in separator 3. Therefore condensate 4 removed from separator 3 is pumped to the elevated rectification pressure by a liquid pump 21. The overhead product 7 of the rectification column, before being mixed with the gaseous fraction in phase separator 3, must be expanded to the latter's pressure, for which a throttle valve 22 is utilized. The thus expanded overhead product is introduced above heat exchanger 20 into separator 3. During the mixing step the condensate formed is separated in separator 3, so that a substantially liquid-free mixture is fed by pipe 10 to turbine 11.

EXAMPLE II

In an embodiment according to FIG. 3, a refinery gas, which contains 20.1% hydrogen, 31.2% methane, 13.2% ethylene, 16.9% ethane, 5.2% propylene, 1.8% propane, 0.9% $C_{4+}$ hydrocarbons, 0.1% sulfur compounds and 10.5% inerts, is fed at a presusre of 16.2 bar and a temperature of 288° K. into the installation by pipe 1. The gas is cooled in heat exchanger 2 to 175° K. and then fed into phase separator 3. The condensate removed by pipe 4 is pumped by pump 32 to the rectification column pressure of 32 bar and fed into column 5, which is operated at an overhead temperature of 180° K. and a bottom temperature of 285° K. The condensate feed stream contains 0.3% hydrogen, 20.1% methane, 26.7% ethylene, 35.0% ethane, 10.9% propylene, 3.8% propane, 1.8% $C_{4+}$ hydrocarbons, 0.2% sulfur compounds and 1.2% inerts. A product stream containing only 70 ppm methane, as well as 33.8% ethylene, 45.0% ethane, 14.0% propylene, 4.8% propane, 2.2% $C_{4+}$ hydrocarbons and 0.2% sulfur compounds is removed by pipe 6. The $C_{2+}$ yield is 96.6% (relative to the $C_{2+}$ content in gas stream 1 that is to be fractionated). The residual overhead gas from the rectification column contains 1.6% hydrogen, 91.0% methane, 2.1% ethylene, 0.3% ethane and 5.0 inerts. It is removed at a temperature of 180° K. by pipe 7, expanded in valve 22 to 16 bar and fed into separator 3. The gas mixture which forms in separator 3 is then expanded in turbine 11 to a pressure of 8.5 bar, at a temperature of 140° K. This cold stream enters heat exchanger 20 where it contacts and is warmed by the gaseous fraction in separator 3, whereupon the expanded gas stream is fed at a temperature of 170° K. to heat exchanger 2 and is heated therein before exiting in pipe 13 at a temperature of 285° K. and a pressure of 7.9 bar.

Figure 4:
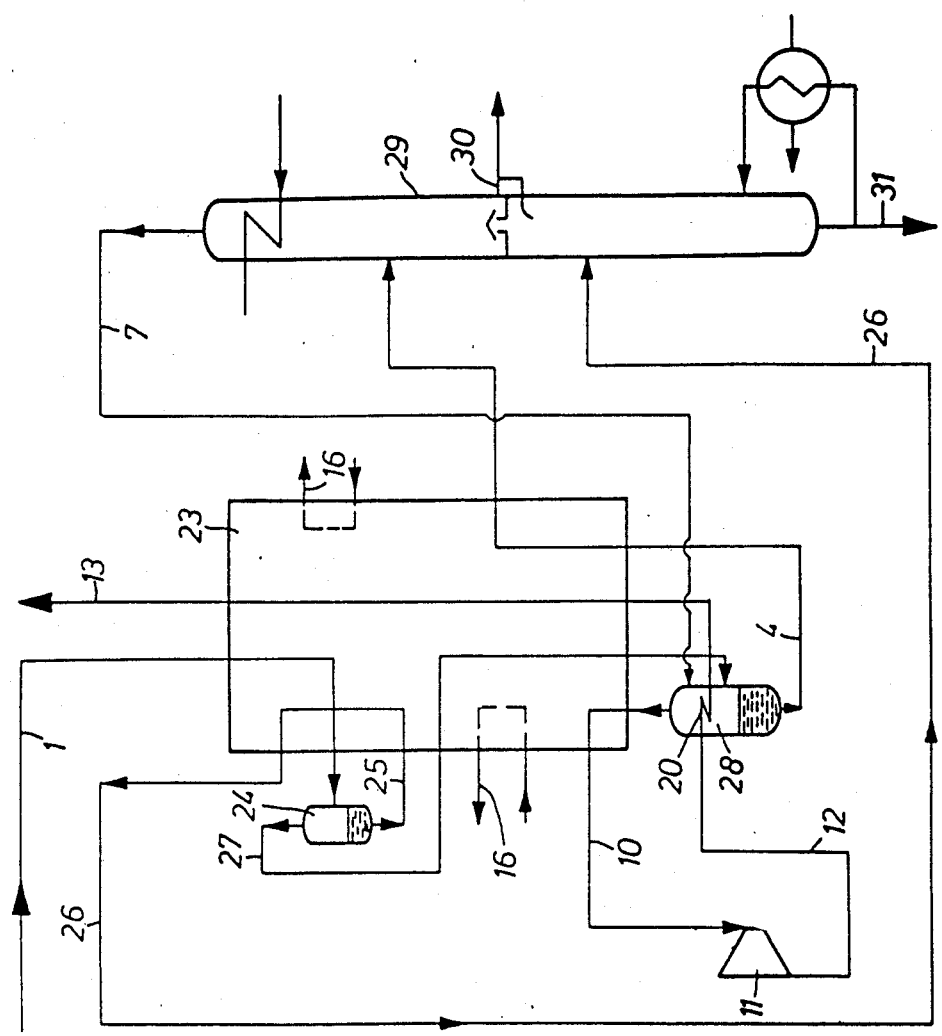

The embodiment shown in FIG. 4 involves yet another embodiment of the process according to the invention, in which the $C_{5+}$ hydrocarbons are separated from the remaining gas mixture. For this purpose, feedstock stream 1 is cooled in a heat exchanger 23 only enough for most of the $C_{5+}$ hydrocarbons to condense, e.g., about 240° to 280° K. The partially cooled mixture at a temperature of 240° to 280° K. is withdrawn from heat exchanger 23, and subjected to a phase separation in a separator 24, whereby the condensed components are separated by pipe 25. The condensate after partial heating, e.g, to about 270° to 330° K., in heat exchanger 23, is fed via conduit 26 to the lower part of a rectification column 29. The remaining gaseous components from the gas stream are removed from separator 24 by pipe 27, again cooled in heat exchanger 23 and finally fed to separator 28 at about 160° to 250° K., which corresponds to separator 3 of the embodiment described in FIG. 3.

Rectification of the condensates separated in separators 24 and 28 takes place in column 29, which, in comparison with the separation column used in the preceding examples, contains a greater number, e.g., about 20 to 50, of theoretical plates. Between the two feed pipes 26 and 4, column 29 features a draw-off conduit 30 at the tray location where the highest $C_3/C_4$ concentration is found. In the bottom of column 29 a liquid bottoms collects which contains $C_{5+}$ hydrocarbons, e.g., about 70 to 100 mol %, and which is removed as product stream at about 370° to 480° K. by pipe 31. A light fraction, which essentially contains $C_1$ and, optionally, $C_2$ hydrocarbons, is removed from the overhead of column 29 by pipe 7, as in the preceding examples.

In this process the heavy components in line 26 which have been separated in separator 24, are also fed to the rectification column at a lower point in the column than line 4. In this way, a very high yield of $C_{3+}$ and $C_{4+}$ hydrocarbons can be attained at relatively small expense.

In the preceding description, by the term "work" is meant thermodynamic external work. It is also conventional to use the term "engine expansion" instead of the term "work expansion".

The preceding examples can be repeated with similar success by substituting the generically or specifically described components and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the separation of $C_{2+}$ or $C_{3+}$ hydrocarbons from a feed gas containing $C_{1+}$ hydrocarbons, in which the feed gas stream being under an elevated pressure is cooled, partially condensed and separated in a phase separator into a liquid and a gaseous fraction, whereupon the gaseous fraction is engine expanded and the liquid fraction is fractionated by rectification into a produce stream containing substantially all $C_{2+}$ or $C_{3+}$ hydrocarbons and a residual gas stream comprising lower boiling components than $C_2$, the improvement comprising passing the residual gas stream into the gaseous fraction resulting from the partial condensation prior to the engine expansion step, and heating engine expanded mixture by indirect heat exchange with the feed gas to be separated.

2. Process according to claim 1, wherein condensate is formed during mixing of the residual gas stream and the gaseous fraction resulting after partial condensation, said process further comprising separating said condensate before the engine expansion of the mixture.

3. A process according to claim 2, wherein the rectification is conducted at a higher pressure than the pressure of the partially condensed gas stream, and further comprising pumping the liquid fraction to the rectification pressure and expanding the residual gas stream formed during rectification into said phase separator to obtain additional condensed liquid from the residual gas fraction.

4. A process according to claim 1, wherein the mixture of the gaseous fraction and the residual gas stream is heated prior to engine expansion to at least above the dew point of the resulting mixture.

5. A process according to claim 4, wherein the rectification takes place at a lower pressure than the pressure of the partially condensed gas stream, and expanding the phase separated gaseous fraction is expanded to the pressure of the residual gas stream.

6. A process according to claim 1, wherein the liquid fraction passing to rectification is at least partially heated against the feed gas stream that is to be cooled.

7. A process according to claim 1, wherein the feed gas stream contains at least 50 mol % of components boiling lower than methane, and further comprising subjecting the feed gas to partial condensation to separate the $C_{1+}$ hydrocarbons before engine expansion of the gaseous fraction.

8. A process according to claim 1, wherein before the formation of the phase separated liquid and gaseous fractions, any $C_{5+}$ hydrocarbons contained in the gas stream are substantially separated therefrom.

9. A process according to claim 8, wherein said rectification is conducted in a rectification column, and further comprising passing the separated $C_{5+}$ hydrocarbons to the rectification column at a location below the entrance of the feed of the liquid fraction formed during partial condensatio, and withdrawing a product stream containing essentially $C_{3-}$ and $C_{4-}$ hydrocarbons from the column at a location between the two feeds.

10. A process according to claim 1, wherein the gaseous fraction resulting after partial condensation is further cooled before being engine expanded by indirect heat exchange with engine expanded gaseous mixture, wherein additional components are condensed and separated therefrom before the engine expansion of resultant gas fraction.

11. A process according to claim 10, wherein the heat exchange between the unexpanded and expanded gaseous fraction is conducted within a mass transfer column having at least two equilibrium stages, in which the separation of the liquid fraction formed during partial condensation is conducted, whereby the partially condensed gas stream is fed in the lower region of the column and the indirect heat exchange between the unexpanded and expanded gaseous fraction is conducted in the upper region of the column.

12. A process according to claim 4, wherein the liquid fraction passing to rectification is at least partially heated against the feed gas stream that is to be cooled.

13. A process according to claim 4, wherein the feed gas stream contains at least 50 mol % of components boiling lower than methane, and further comprising subjecting the feed gas to partial condensation to separate the $C_{1+}$ hydrocarbons before engine expansion of the gaseous fraction.

14. A process according to claim 6, wherein the feed gas stream contains at least 50 mol % of components boiling lower than methane, and further comprising subjecting the feed gas to partial condensation to separate the $C_{1+}$ hydrocarbons before engine expansion of the gaseous fraction.

15. A process according to claim 12, wherein the feed gas stream contains at least 50 mol % of components boiling lower than methane, and further comprising subjecting the feed gas to partial condensation to separate the $C_{1+}$ hydrocarbons before engine expansion of the gaseous fraction.

16. A process according to claim 4, wherein the gaseous fraction resulting after partial condensation is further cooled before being engine expanded by indirect heat exchange with engine expanded gaseous mixture, wherein additional components are condensed and separated therefrom before the engine expansion of resultant gas fraction.

17. A process according to claim 7, wherein the gaseous fraction resulting after partial condensation is further cooled before being engine expanded by indirect heat exchange with engine expanded gaseous mixture, wherein additional components are condensed and separated therefrom before the engine expansion of resultant gas fraction.

18. A process according to claim 13, wherein the gaseous fraction resulting after partial condensation is further cooled before being engine expanded by indirect heat exchange with engine gaseous mixture, wherein additional components are condensed and separated therefrom before the engine expansion of resultant gas fraction.

19. A process according to claim 14, wherein the gaseous fraction resulting after partial condensation is further cooled before being engine expanded by indirect heat exchange with engine expanded gaseous mixture, wherein additional components are condensed and separated therefrom before the engine expansion of resultant gas fraction.

20. A process according to claim 15, wherein the gaseous fraction resulting after partial condensation is further cooled before being engine expanded by indirect heat exchange with engine expanded gaseous mixture, wherein additional components are condensed and separated therefrom before the engine expansion of resultant gas fraction.

21. A process according to claim 1, wherein said liquid fraction is directly expanded into a rectification column.

22. A process according to claim 1, wherein said liquid fraction is directly pumped into a rectification column.

23. A process according to claim 1, wherein said engine expanded mixture is removed as a gas product after indirect heat exchange with said feed gas.

24. A process according to claim 1, wherein said residual gas stream substantially comprises lower boiling components than $C_2$.

25. A process according to claim 1, wherein said feed gas is cooled to a temperature of about 160 to 235K.

* * * * *